(12) United States Patent
Malige et al.

(10) Patent No.: US 6,375,838 B1
(45) Date of Patent: Apr. 23, 2002

(54) SEALED TANKS FOR METHANE FERMENTATION OR STORAGE IN A CORROSIVE ENVIRONMENT

(75) Inventors: Jean Malige, Courbevoie; Patrick Suhr, Rueil Malmaison, both of (FR)

(73) Assignee: Degremont, Rueil Malmaison (FR)

( * ) Notice: Subject to any disclaimer, the term of this patent is extended or adjusted under 35 U.S.C. 154(b) by 0 days.

(21) Appl. No.: 09/674,557

(22) PCT Filed: Apr. 22, 1999

(86) PCT No.: PCT/FR99/00962

§ 371 Date: Jan. 17, 2001

§ 102(e) Date: Jan. 17, 2001

(87) PCT Pub. No.: WO99/58458

PCT Pub. Date: Nov. 18, 1999

(30) Foreign Application Priority Data

May 13, 1998 (FR) .............................................. 98 06030

(51) Int. Cl.[7] ................................................. C02F 3/28

(52) U.S. Cl. ....................................................... 210/188
(58) Field of Search ......................................... 210/188

(56) References Cited

FOREIGN PATENT DOCUMENTS

GB        2162195 A   *   1/1986

* cited by examiner

*Primary Examiner*—Chester T. Barry
(74) *Attorney, Agent, or Firm*—Connolly Bove Lodge & Hutz LLP

(57) ABSTRACT

A sealed tank includes a concrete footing, a steel or concrete shell ring and a sealed and corrosion-resistant dome having a double membrane. There is an inner membrane delimiting, with the surface of the liquid effluent contained in the shell ring, a sealed chamber intended to receive biogas that results from the methane fermentation or from a corrosive environment. An outer membrane envelopes the inner membrane and which, when pressurized, applies a given pressure to the volume of biogas or of corrosive environment contained in the chamber.

3 Claims, 2 Drawing Sheets

SEALED TANKS FOR METHANE FERMENTATION OR STORAGE IN A CORROSIVE ENVIRONMENT

FIELD OF THE INVENTION

The present invention relates to a device for protecting constructions for the treatment of sludges or waste water, and is aimed more particularly at a device for protecting the parts of a methane fermentation or storage construction in contact with a corrosive environment.

This invention is particularly applicable to sealed chambers or tanks in which methane fermentation treatments are performed on liquid effluents at various concentrations. It is known that methane fermentation, sometimes known as "digestion", is a bacterial process that treats the organic matter of the following kinds of effluent: sludges from purification stations, swine manure from pig farms, urban waste water or water from industrial processes. The ultimate purpose of the methane fermentation varies widely: the production of methane for use as energy, the stabilization of fermentation, the reduction of the mass of organic matter, the reduction of carbon-containing pollutants for compliance with standards prior to discharge into the environment, etc.

A methane fermentation chamber or digester is generally in the form of a sealed tank comprising a concrete base on which there rests a steel or concrete shell ring covered by a dome, the said tank being filled with a sludge or manure liquor.

The bacterial processes carried out in these methane fermentation chambers or digesters produce a biogas made up essentially of methane and carbon dioxide, but also containing corrosive gases including, in particular, hydrogen sulphide. It is therefore necessary for the materials of which the methane fermentation constructions or digesters are made (common steels and concrete) to be sealed against the corrosive gases and for them to be able to withstand the corrosion that these cause.

At the present time, surfaces of a construction in contact with corrosive gases are protected by coatings of epoxy pitch, polyurethane or other equivalent painted-on treatments. These coatings have a number of drawbacks and so, in the case of concrete constructions:

- there is the need to apply the coating to perfectly dry concrete, this resulting in a waiting time of 28 days after the civil engineering work has been completed,
- there is the need to prepare the entire surface in order to remove any chalking and in order to repair any imperfections in the stonework,
- there is the need, because of the enclosed nature of the construction, to install a sizeable air renewal system and to operate with a solvent-free paint,
- there is the need for rigorous use of protective clothing when using epoxy pitch, contact with which is dangerous. An increasing number of countries are banning this substance because of this. Polyurethane involves fewer restrictions, but is more expensive,
- there is the risk of the coating becoming torn and the protection therefore becoming ruined if the concrete cracks by a few tenths of a millimeter,
- there is a risk that the coating will lift through the ingress of moisture into the concrete from unprotected surfaces.

In the case of steel constructions, the constraints on renewing the air and protecting the person applying the coating are the same. What is more, there is also the need to peen the surface before this kind of paint coating can be applied.

A steel construction can also be protected by the use of glazed steel sheet. Aside from its higher cost, this technique demands special precautions throughout the duration of the work, so as to avoid any cracking in the layer of glass. In addition, the difference in expansion that there is between steel and glass leads to a risk of cracking in heated buildings, this being of particular concern in the case of methane fermentation constructions operating at 35° C. Finally, the mastic seals used to seal the joins between the sheets are not good at resisting corrosion from the gases.

It has therefore become perfectly apparent that, in the prior art, producing a device for protecting methane fermentation constructions is awkward and involves a number of uncertainties detrimental to the life of the constructions.

In another field, there are flexible gas holders for storing the biogas that results from the methane fermentation processes. These gas holders are fixed to a concrete footing and consist of a double membrane: an inner membrane producing a sealed chamber intended to receive the biogas, and an outer membrane enveloping the inner membrane and which, when pressurized, applies a given pressure to the volume of biogas contained in the inner membrane. These flexible gas holders can also be installed directly on a conventional digester of the type specified hereinabove, in place of the dome.

GB-A-2 162 195 describes a fixing for a membrane for a fermentation reactor, of the gas holder type, employing an inflatable bulge inserted in a metal profile section. This publication of the prior art does not envisage means for providing a seal between the metal profile section and the wall of the reactor and, this being the case, the problem resulting from the corrosion due to the corrosive gas is not solved.

BRIEF DESCRIPTION OF THE INVENTION

Starting from this state of the art, the present invention proposes to produce a methane fermenter/digester covered with a dome of the flexible gas holder type in which the shell ring of the methane fermenter/digester is protected by means which are economical and reliable over time.

The present invention proposes to provide a solution to the problems of the devices of the prior art recalled hereinabove, by setting itself as objectives to avoid the use of a corrosion-proof coating on those parts of the construction which are exposed to the corrosive environment and also to eliminate the need to make a seal between the upper part of the shell ring and the means intended for covering the latter, particularly a sealed double membrane.

In consequence, the subject of this invention is a sealed tank intended for carrying out methane fermentation treatments on liquid effluent such as sludges, manures, urban or industrial effluents, for example, or for storing a medium in a corrosive environment, comprising a concrete footing, a steel or concrete shell ring and a sealed and corrosion-resistant dome consisting of a double membrane: an inner membrane delimiting, with the surface of the liquid effluent contained in the said shell ring, a sealed chamber intended to receive the biogas that results from the methane fermentation, or the said corrosive environment, and an outer membrane enveloping the inner membrane and which, when pressurized, applies a given pressure to the volume of biogas or of corrosive environment contained in the said chamber, the said sealed tank being characterized in that the said inner membrane is extended downwards by a skirt, the lower part of which is submerged below the level of liquid effluent contained in the tank so as thus to seal the chamber delimited above the said level, the said skirt being fixed, around its entire periphery, below the level of liquid effluent, to the interior wall of the said shell ring by a seal pressed against the said wall, using flat stainless steel bars which are fixed into the wall, it being possible, for example, for this fixing to be achieved using bolts, fitted with sealing washers known as "bonded seal" washers.

According to the invention, the said seal is preferably made of a synthetic material, such as neoprene in particular.

Other features and advantages of the invention will become apparent from the description given hereinafter with reference to the appended drawing which illustrates one exemplary embodiment thereof, with no limitation implied.

DETAILED DESCRIPTION OF THE INVENTION

Figure 1:
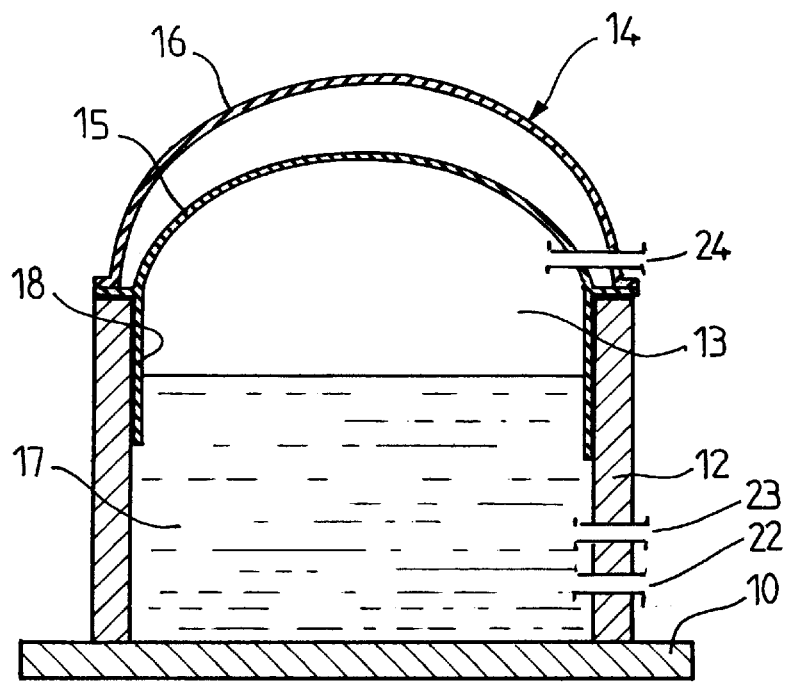
FIG. 1 is a diagrammatic view in vertical section depicting a digester according to the present invention.

Referring to FIG. 1, this depicts a construction for methane fermentation employing the present invention. This construction comprises, in the known way, a concrete footing 10 and a steel or concrete shell ring 12 which is covered by a double membrane made of a sealed and corrosion-resistant material, denoted in its entirety by the reference 14. This double membrane is made up of an inner membrane 15 which, with the shell ring 12, delimits a chamber 13, sealed against the biogas contained above the liquid effluent 17 contained in the volume defined by the shell ring, and an outer membrane 16 enveloping the inner membrane 15, the said membrane 16 differing from the inner membrane 15. As in the prior-art solutions employing such a double membrane, the outer membrane is pressurized. Sludge or effluent is fed in or extracted via passages 22 and 23 sealed into the shell ring. Biogas itself is extracted at a sealed passage 24 sandwiching the membranes 15 and 16.

According to the present invention, the lower membrane 15 is extended by a circular skirt 18, also sealed and corrosion-resistant, the said skirt 18 covering the internal surface of the construction from the top of the shell ring 12 down to a determined distance below the minimum level of the liquid effluent 17 so as to ensure complete sealing between the shell ring 12 and the "head" of corrosive gas contained in the chamber 13. By way of non-limiting example, it may be mentioned that the distance separating the lower part of the skirt 18 from the minimum level of liquid may be of the order of 1 meter.

Figure 2:
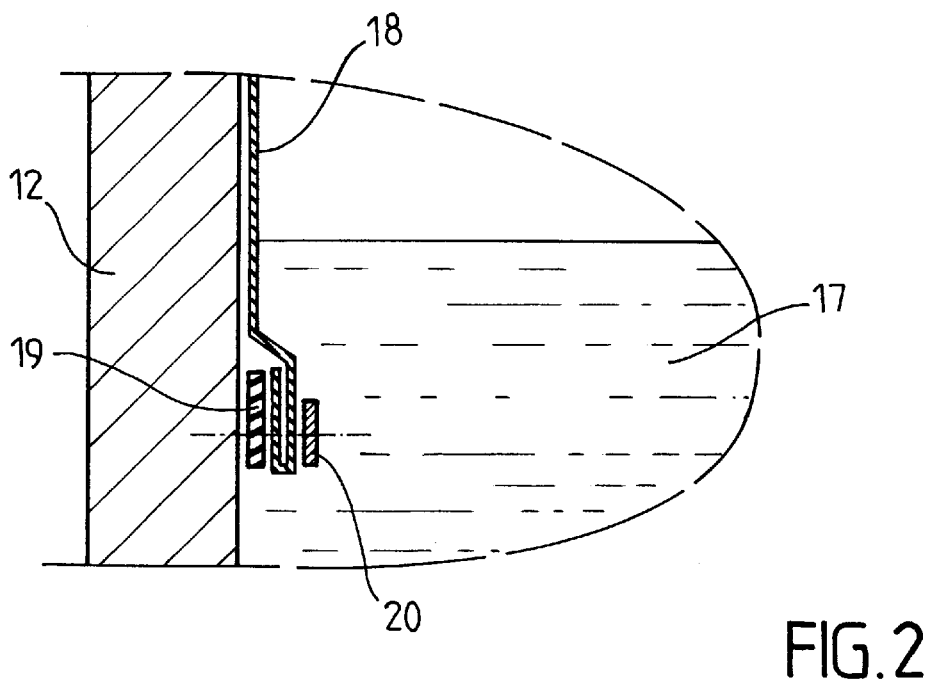
FIGS. 2 and 3 are detailed views, also in vertical section on a larger scale, illustrating two exemplary embodiments of means envisaged by the invention for positioning and fixing the skirt of the inner membrane on the shell ring of the tank.

According to the present invention, the membrane may be held in position by fitting a seal between the lower part of the skirt 18 and the shell ring 12. FIG. 2 illustrates a non-limiting exemplary embodiment of such a seal. It consists in this instance of a circular ring, preferably of synthetic material, particularly neoprene, 19 which is kept pressed along the interior wall of the shell ring 12 using flat stainless steel bars such as 20, bolted into the said wall, using sealing washers of the "bonded seal" washer type, for example. It would of course be possible to use other means to allow the membrane to be held in position such that the lower part of the skirt was always located below the level of liquid effluent 17 contained in the shell ring.

Figure 3:
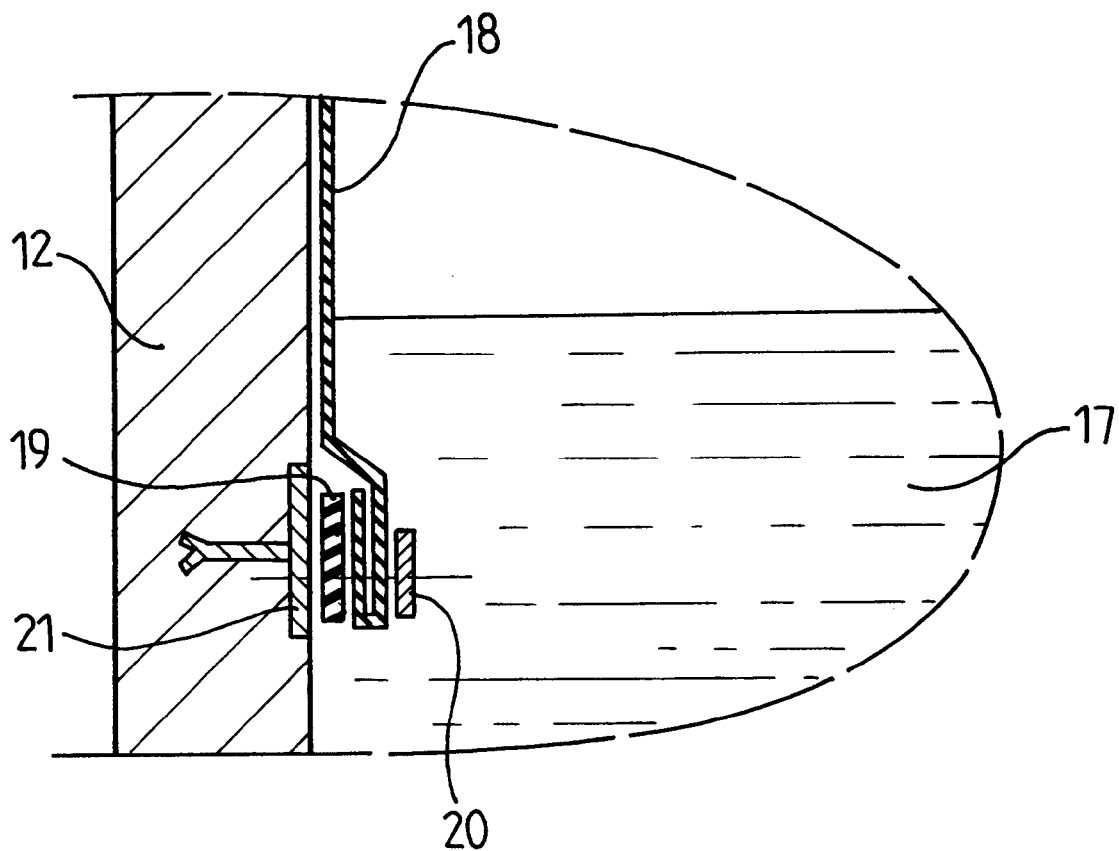

In the alternative form illustrated by FIG. 3, the skirt 18 is furthermore fixed to the interior wall of the shell ring 12 using a metal ring 21 which is inserted into the shell ring and to which the skirt is fixed.

It is evident from reading the description given hereinabove that the invention does effectively provide a solution to the problems posed by the presence of corrosive gases in methane fermentation constructions or storage constructions, while at the same time eliminating the need to envisage a protective coating on those parts of the construction which are in contact with the corrosive gases and at the same time eliminating the problems of sealing which has to be achieved at the top of the shell ring, as sealing in the device according to the invention is provided by the presence of the skirt which extends below the liquid level, the invention envisaging the lower membrane being held in position and sealed by any appropriate means.

This results in the following advantages, in the phases of building and of operating the constructions:

the fixing to the wall of the construction can be performed regardless of the surface finish of the steel, or of the surface condition or dampness of the concrete, the handling of and contact with the skirt are free of risk; no special renewal of air needs to be performed;

any cracking of the concrete will have no impact on the ability of the skirt to afford protection, as this is totally independent;

the elasticity of the textile makes it possible for all phenomena of differential expansion to be absorbed.

It must remain clearly understood that the present invention is not restricted to the exemplary embodiment and application described and/or depicted but that it encompasses all variations thereof which fall within the context and scope of the appended claims.

What is claimed is:

1. A sealed tank containing a liquid effluent and a methane fermentation biogas, comprising: a concrete footing, a steel or concrete shell ring and a sealed and corrosion-resistant dome including an inner membrane delimiting a sealed chamber containing the biogas corrosive environment, and an outer membrane enveloping the inner membrane and which, when pressurized, applies a given pressure to the volume of biogas or of corrosive environment contained in said chamber, said inner membrane extended downwardly by a skirt, the lower part of which is submerged below the level of the liquid effluent so as to seal the chamber above said level, the skirt being fixed, around its entire periphery, below the level of liquid effluent, to the interior wall of the shell ring by a seal pressed against the wall, using flat stainless steel bars which are fixed into the wall.

2. The tank according to claim 1, wherein flat bars are fixed into the interior wall of the shell ring using bolts fitted with sealing washers.

3. The tank according to claim 1, further comprising a metal ring inserted into said shell ring and to which the skirt is fixed.

\* \* \* \* \*